United States Patent
O'Lenick et al.

(10) Patent No.: US 7,790,813 B2
(45) Date of Patent: *Sep. 7, 2010

(54) MULTIFUNCTIONAL SILICONE RESIN POLYMERS

(75) Inventors: Kevin Anthony O'Lenick, Dacula, GA (US); Anthony J. O'Lenick, Jr., Dacula, GA (US)

(73) Assignee: Siltech LLC, Dacula, GA (US)

( * ) Notice: Subject to any disclaimer, the term of this patent is extended or adjusted under 35 U.S.C. 154(b) by 276 days.

This patent is subject to a terminal disclaimer.

(21) Appl. No.: 12/220,786

(22) Filed: Jul. 29, 2008

(65) Prior Publication Data

US 2010/0029863 A1    Feb. 4, 2010

(51) Int. Cl.
*C08F 283/12* (2006.01)
*C08G 77/12* (2006.01)

(52) U.S. Cl. .................. 525/479; 528/19; 528/26.5; 528/31; 528/32; 528/33

(58) Field of Classification Search .................. 525/479
See application file for complete search history.

(56) References Cited

U.S. PATENT DOCUMENTS

| | | | | |
|---|---|---|---|---|
| 5,663,042 A | * | 9/1997 | Grieve et al. | 430/619 |
| 5,741,552 A | * | 4/1998 | Takayama et al. | 427/407.1 |
| 6,191,215 B1 | * | 2/2001 | Beckham et al. | 524/731 |
| 6,258,913 B1 | * | 7/2001 | Herzig et al. | 528/15 |
| 6,784,271 B2 | * | 8/2004 | Nakanishi | 528/25 |
| 7,019,098 B2 | | 3/2006 | Hupfield | |
| 7,413,744 B2 | * | 8/2008 | Ichinohe | 424/401 |
| 7,632,488 B1 | * | 12/2009 | O'Lenick, Jr. | 424/70.12 |
| 2008/0108842 A1 | * | 5/2008 | Pafford et al. | 556/439 |

FOREIGN PATENT DOCUMENTS

EP    163825 A2 * 12/1985

* cited by examiner

*Primary Examiner*—Randy Gulakowski
*Assistant Examiner*—Mike Dollinger

(57) ABSTRACT

The present invention relates to a series of crosslinked silicone polymers that by virtue of the nature of the dimol alcohol undecylenic acid ester based crosslinker, have unique solubility and properties. These include improved tolerance for oily materials and improved skin feel. These polymers find use in personal care applications like pigmented products. In the personal care arena, solid products that do not experience syneresis are important. Syneresis is a condition that exists in a solid product that causes a liquid that is incompatible to ooze out, which is cosmetically unacceptable.

9 Claims, No Drawings

MULTIFUNCTIONAL SILICONE RESIN POLYMERS

FEDERAL SPONSORSHIP

None

FIELD OF THE INVENTION

The present invention relates to a series of crosslinked silicone/fatty complex ester polymers that by virtue of the nature of the crosslinker have unique solubility and properties. These include improved tolerance for oily materials and water soluble materials. These polymers find use in personal care applications like pigmented products. In the personal care arena, solid products that do not experience syneresis are important. Syneresis is a condition that exists in a solid product that causes a liquid that is incompatible to ooze out, which is cosmetically unacceptable.

BACKGROUND OF THE INVENTION

The term silicone resin has been applied both to and misapplied to a variety of materials over time. Silicone resins as used herein refer to a series of products which include at least two silicone backbones that are joined by a "crosslinking group". The number of crosslinking groups that are present as a percentage of the total molecular weight will determine the properties of the resulting polymer.

If there are no crosslinking groups; the polymer can freely rotate and consequently is an oily liquid. If a few crosslinking groups are introduced, the ability to rotate is slightly restricted and the oily material becomes "rubbery". The rubbery material should be referred to as an elastomer. The properties are morel like a rubber band than plastic. As the percentage of crosslinking increases still the molecule becomes rigid. This class of compounds are resins. If you hit the film with a hammer and it shatters it is a resin, if it bounces it is an elastomer and if it squirts out is a silicone fluid.

The difficulty in determining if a product is a fluid an elastomer or resin occurs for products that lie between the classifications. Specifically, when does an elastomer become a resin? While this exact point is of academic interest it does not have nay practical significance to the present invention.

There are a number of classes of resin compounds differing in the nature of the crosslinker. One class is the so called "Q resins".

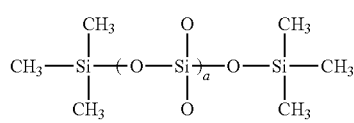

The oxygen that needs another bond connects to another polymer as shown:

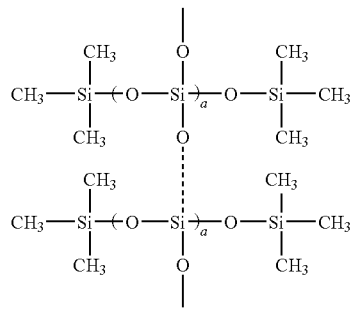

The crosslinking group is —O—. This type of resin is disclosed in U.S. Pat. No. 6,139,823, incorporated herein by reference. This type of material has a group, the so called "Q" group in which a Si has four oxygen atoms attached. In the above case it is the group that is within the "a" subscript. This type of resin is very powdery and is rarely used without a plasticizer. This class of compounds can also dry the skin.

The next class of resin contain alkyl connecting groups.

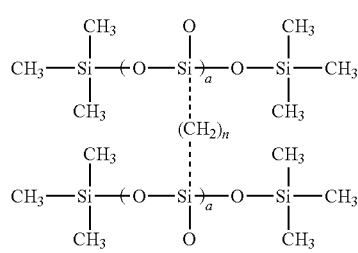

In the case where n=1 acetylene is used as a crosslinking reactant. It is reacted with a silanic hydrogen polymer. As n is increased the reactant is an alpha omega divinyl compound.

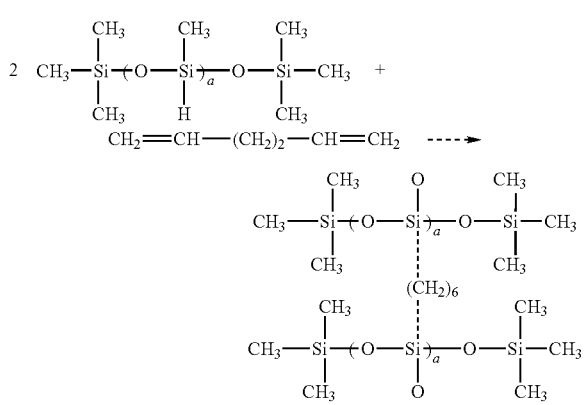

The reaction is called hydrosilylation and provides the linking groups between the molecules. The reaction is generally run in solvent like cyclomethicone (D4 or D5 or hexamethyl disiloxane) or in volatile organic like isododecane. A catalyst generally a platinum one is used to effect the reaction. Chloroplatinic acid or Karnsteadt catalyst are preferred. The resulting material is a viscous liquid that when the solvent evaporates provides a film.

The present invention makes use of novel crosslinking reagents that provide groups that significantly alter the solubility of the resin. This is done by introducing fatty ester linkages, water soluble groups linked with fatty esters and glyceryl esters. Not only does the solubility change, the ability to formulate solid products free from syneresis also occurs. Another unexpected benefit is that the ester moiety provides improved biodegradation of the resin making the resin "more green" and improving consumer acceptability. None of these advantageous are present in the compounds known heretofore.

THE INVENTION

Object of the Invention

It is the object of the present invention to provide a series of silicone polymers that make use of a unique fatty multifunctional crosslink compound. This compound is very efficient in reacting with a variety of silanic hydrogen containing polymers to provide a crosslinked product. The crosslinker is an undecylenic ester of pentaerythritol, and trimethylol propane.

Another object of the present invention is to provide a series of products suitable for formulation into personal care products providing improved skin feel (i.e. not drying like Q resins) and having improved solubility over alkyl linked polymers.

Other objects of the invention will become clear as one reads the specification attached hereto.

All % given herein are % by weight, all temperatures are ° C., all patents and publications referred to herein are incorporated herein by reference in their entirety as appropriate.

SUMMARY OF THE INVENTION

The present invention relates to a series of silicone resins that provide improved oil solubility and film forming properties when reacted into resin systems; that are soluble in organic oils including triglycerides, esters and other non-silicone materials.

The compounds of the present invention are made by reacting specific multifunctional undecylenic esters with silicone compounds that contain multiple silanic hydrogen (Si—H) groups. The reaction is conducted in a suitable solvent including esters, triglycerides and other non-volatile oils.

DETAILED DESCRIPTION OF THE INVENTION

Resins of the present invention are a class of silicone compounds which are prepared by the reaction of a poly-vinyl compound reacted with a silanic hydrogen containing compound.

Reaction 1

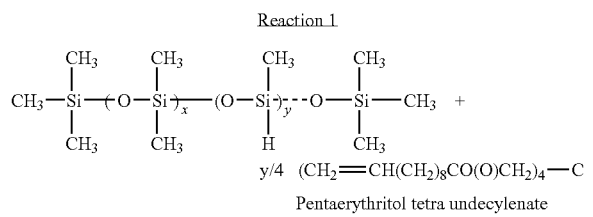

Pentaerythritol tetra undecylenate

The resulting polymer is a tetra functional tetra C11 alkyl ester compound. The first step is the reaction of the SiH and the first vinyl group to make:

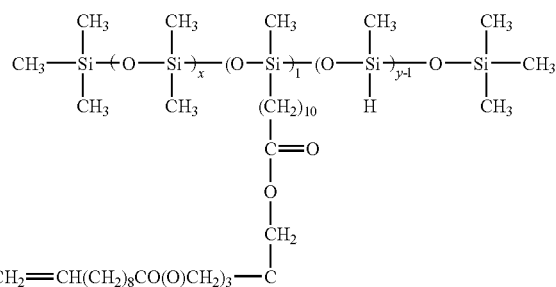

wherein:
x is an integer ranging from 0 to 2000;
y is an integer ranging from 4 to 200.

Subsequently (or concurrently) the remaining Si—H groups react with the remaining vinyl groups to make crosslinked polymers. There are at least four Si—H groups and four vinyl groups to react. There is no obvious group specificity, so there is no more likelihood for the vinyl to react with another SiH in the first silicone (already bearing an organic group) than to react with a different silicone polymer containing SiH (without any organic group). The result is a crosslinked polymer. Said polymer has a C11 group connected via an ester group with a methylene group connected to a central carbon connected to three other methylene groups connected through an ester to a C11 group connected to a silicone polymer.

The second reaction sequence is one in which there are only three such undecylenic groups. That is one group is replaced with an ethyl group.

Reaction 2

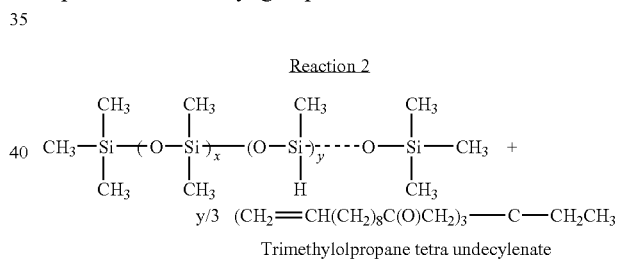

Trimethylolpropane tetra undecylenate wherein:
x is an integer ranging from 0 to 200;
y is an integer ranging from 4 to 20.

Exactly the same sequence occurs only this time there are just three ester groups and an ethyl group around the central carbon.

The reactions are typically carried out in an ester, a triglyceride or other non-volatile, non-silicone containing solvent. The presence of the multiple C11 groups in the ester makes the compounds soluble in these more polar oils and provides a soluble resin. A suitable hydrosilylation catalyst like chloroplatinic acid or Karnstedt catalyst is used.

Crosslinker

We have surprisingly and unexpectedly found that the undecylenate di-ester of pentaerythritol or trimethylolpropane are surprisingly good crosslinkers when making organosoluble silicone resins.

Pentaerythritol is a commercially available material conforming to the following structure:

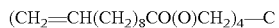

CAS 115-77-5
INECS NO. 2004-104-9.
FORMULA, C(CH$_2$OH)$_4$
Other name: 2,2-Bis(hydroxymethyl)1,3-propanediol Trimethylolpropane is a commercially available material which conforms to the following structure:

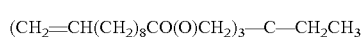
(CH$_2$=CH(CH$_2$)$_8$CO(O)CH$_2$)$_3$—C—CH$_2$CH$_3$

CAS Number 77-99-6
EINECS Number: 201-074

Other names include: 2-Ethyl-2-(hydroxymethyl)-1,3-propanediol 9Trimethylol propane; propylidynetrimethanol; 1,1,1-Tris(hydroxymethyl)propane; Ethriol; Ethyltrimethylolmethane; Hexaglycerine; 2,2-Bis(hydroxymethyl)-1-butanol; Propylidintrimethanol (German); Propilidintrimetanol (Spanish); Propylidynetrimédthanol (French)/

This crosslinker is made by the transesterification reaction of undecylenic methyl ester with either pentaerythritol, trimethylolpropane or mixtures thereof. Undecylenic acid is an item of commerce. It conforms to the following structure:

CH$_2$=CH—(CH$_2$)$_8$C(O)OCH$_3$

CAS 103-26-4
EINECS 227-279-3

The undecylenic acid esters are one aspect of the present invention. The product is made by a transesterification reaction which is carried out at temperatures of between 150° C. and 220° C. Esterification catalysts can be added as required. An excess of methyl undecylenate is used at 2:1 and after the reaction is complete the excess is removed using vacuum. Methyl undecylenate boils at 160 C at a pressure of 50 mm Hg. Unlike using the acid which has a high boiling point an excess is use to drive the reaction and the excess is stripped off. This approach allows for a high purity product with no acid value and no need for tin catalyst which hinders the subsequent polymerization.

Crosslinker Synthesis

Example 1

To 34.0 grams of pentaerythritol is added 400.0 grams of methyl undecylenate. The reaction mixture is heated to 200 C and held to collect methanol. Once the amount of methanol reaches theoretical, vacuum is applied to remove residual methyl undecylenate. The resulting product conforms to the following structure and is used without additional purification. (CH$_2$=CH(CH$_2$)$_8$CO(O)CH$_2$)$_4$—C Example 2

To 44.7 grams of trimethylolpropane is added 400.0 grams of methyl undecylenate. The reaction mixture is heated to 200 C and held to collect methanol. Once the amount of methanol reaches theoretical, vacuum is applied to remove residual methyl undecylenate. The resulting product conforms to the following structure and is used without additional purification. (CH$_2$=CH(CH$_2$)$_8$CO(O)CH$_2$)$_3$—CH$_2$CH$_3$ The second reactant is a silanic hydrogen containing compound, which is an item of commerce commercially available from Siltech Corporation Toronto Canada, conforming to the following structure:

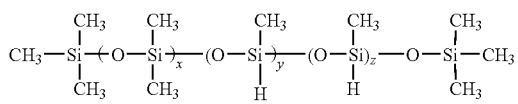

The present invention relates to a series of compounds made by the hydrosilylation reaction of a silanic hydrogen containing silicone conforming to the following structure:

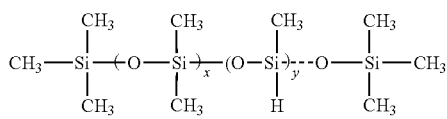

wherein;

x is an integer ranging from 0 to 200;

y is an integer ranging from 2 to 20;

with an undecylenic ester compound selected from the group consisting of

(CH$_2$=CH(CH$_2$)$_8$CO(O)CH$_2$)$_3$—CH$_2$CH$_3$ and

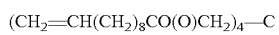
(CH$_2$=CH(CH$_2$)$_8$CO(O)CH$_2$)$_4$—C in the presence of a suitable hydrosilylation catalyst.

Preferred Embodiments

In a preferred embodiment the undecylenic ester is

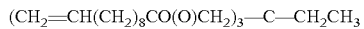
(CH$_2$=CH(CH$_2$)$_8$CO(O)CH$_2$)$_3$—C—CH$_2$CH$_3$

In a preferred embodiment the undecylenic ester is

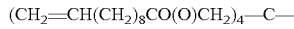
(CH$_2$=CH(CH$_2$)$_8$CO(O)CH$_2$)$_4$—C—

In a preferred embodiment x is an integer ranging from 1 to 200; and y is an integer ranging from 4 to 20.

In a preferred embodiment x is an integer ranging from 1 to 10; and y is an integer ranging from 4 to 10.

In a preferred embodiment x is an integer ranging from 1 to 10 and y is an integer ranging from 4 to 10.

In a preferred embodiment x is 0; and y is an integer ranging from 4 to 10.

EXAMPLES

Silanic Hydrogen Silicone Compounds

Examples 3-13

Silanic Hydrogen compounds are items of commerce made by a variety of suppliers, including Siltech Corporation in Toronto Canada. They conform to the following structure:

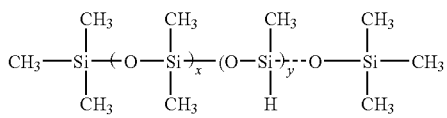

The values of "x" and "y" were determined by Si29 NMR.

| Example | X | Y |
|---|---|---|
| 3 | 0 | 2 |
| 4 | 10 | 5 |
| 5 | 15 | 20 |
| 6 | 25 | 50 |
| 7 | 50 | 25 |
| 8 | 75 | 15 |
| 9 | 100 | 28 |
| 10 | 5 | 5 |
| 11 | 10 | 15 |
| 12 | 6 | 10 |
| 13 | 200 | 20 |

Hydrosilylation Compounds of the Present Invention

Hydrosilylation Solvents

Examples 14-16

The hydrosilylation reactions are advantageously run in a volatile solvent, which can later be distilled off is desired. It is also a practice to sell the products in solvent.

| Example | Description |
|---|---|
| 14 | soybean oil |
| 15 | Pentaerythritol tetra C8C10 |
| 16 | isopropyl myristate |

Hydrosilylation

Hydrosilylation is a process that reacts terminal vinyl compounds with silanic hydrogen to obtain a Si—C bond. References to this reaction, incorporated herein by reference, include:

U.S. Pat. Nos. 3,715,334 and 3,775,452 to Karstedt, shows the use of Pt(O) complex with vinylsilicon siloxane ligands as an active hydrosilylation catalyst.

Additional platinum complexes, such as complexes with platinum halides are shown by, U.S. Pat. No. 3,159,601 Ashby and, U.S. Pat. No. 3,220,972, to Lamoreaux.

Another hydrosilylation catalyst is shown by Fish, U.S. Pat. No. 3,576,027. Fish prepares a platinum(IV) catalyst by reacting crystalline platinum(IV) chloroplatinic acid and organic silane or siloxane to form a stable reactive platinum hydrosilylation catalyst.

General Procedure

To the specified number of grams of the specified solvent (Examples 14-16) is added the specified number of grams of the specified silanic hydrogen compound (Example 3-13). The mass is mixed well. To that mixture is added the specified number of grams of the specified undecylenate ester (Example 1 or 2). To that mixture is added 0.01% Karstedt catalyst, which is commercially available from Geleste. The agitation is stopped and the reaction begins with an exotherm.

The reaction mass will thicken over 4 hours, but most rapidly in the first twenty minutes. Once the maximum viscosity is reached the reaction is considered complete. The solvent may be distilled off or the product may be sold as prepared without additional purification.

| Polymers (Examples 17-27) | | | | | |
|---|---|---|---|---|---|
| Example 1 | | Silanic Hydrogen | | Solvent | |
| Example | Grams | Example | Grams | Example | Grams |
| 17 | 203.0 | 3 | 142.0 | 14 | 690.0 |
| 18 | 203.0 | 4 | 240.0 | 15 | 443.0 |
| 19 | 203.0 | 5 | 94.0 | 16 | 648.0 |
| 20 | 203.0 | 6 | 100.0 | 14 | 303.0 |
| 21 | 203.0 | 7 | 215.0 | 15 | 800.0 |
| 22 | 203.0 | 8 | 441.0 | 16 | 640.0 |
| 23 | 203.0 | 9 | 330.0 | 14 | 1000.0 |
| 24 | 203.0 | 10 | 167.0 | 15 | 370.0 |
| 25 | 203.0 | 11 | 120.0 | 16 | 500.0 |
| 26 | 203.0 | 12 | 121.0 | 14 | 325.0 |
| 27 | 203.0 | 13 | 142.0 | 15 | 650.0 |

| Polymers (Examples 27-27) | | | | | |
|---|---|---|---|---|---|
| Example 1 | | Silanic Hydrogen | | Solvent | |
| Example | Grams | Example | Grams | Example | Grams |
| 27 | 210.0 | 3 | 142.0 | 15 | 700.0 |
| 28 | 210.0 | 4 | 240.0 | 14 | 450.0 |
| 29 | 210.0 | 5 | 94.0 | 16 | 650.0 |
| 30 | 210.0 | 6 | 100.0 | 16 | 300.0 |
| 31 | 210.0 | 7 | 215.,0 | 14 | 800.0 |
| 32 | 210.0 | 8 | 441.0 | 16 | 650.0 |
| 33 | 210.0 | 9 | 330.0 | 15 | 950.0 |
| 34 | 210.0 | 10 | 167.0 | 15 | 370.0 |
| 35 | 210.0 | 11 | 120.0 | 14 | 0 |
| 36 | 210.0 | 12 | 121.7 | 16 | 500.0 |
| 37 | 210.0 | 13 | 142.0 | 15 | 650.0 |

The key to understanding the functionality of the resin of the present invention is an appreciation that silicone and oil are mutually immiscible groups. This lack of solubility is the cause of the syneresis (or separation) seen in pigmented products that contain oil, and silicone. If the molecule has these groups properly connected the molecule will orientate itself into the lowest free energy. In this configuration the oil loving and silicone portions of the resin and of the formulation will all associate in a matrix. The parts of this linking group that connect to the silicone group are oil soluble. The length of that group is fairly long and symmetrical. The internal group is water loving (polar). Resins with this configuration allows for the incorporation of both oil loving (non-polar non-silicone) and silicone loving components in the formulation. This produces an emollient property to the skin in a film forming matrix. The presence of the ester group helps biodegradability.

Applications

The resins of the present invention can be used in personal care products for a variety of applications including hair and skin care. Applied to hair, they provide conditioning effects and gloss. Applied in pigmented compositions they provide transfer resistance and pigment uniformity. Applied in mascara they provide ease of application and good film properties.

The ability to modify the properties of the resin to achieve particular properties is highly desirable. The higher the "x" value relative to the "y" value in the product the more silicone loving the material. The higher the "y" value relative to the "x" value the more oil loving the material. The materials based upon pentaerythritol are more plastic like or resinous than the same materials made from trimethylol propane.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

We claim:

1. A silicone resin made by the hydrosilylation reaction of a silanic hydrogen containing silicone conforming to the following structure:

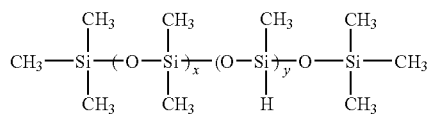

wherein;
x is an integer ranging from 0 to 200;
y is an integer ranging from 4 to 20;
with an undecylenic ester compound selected from the group consisting of

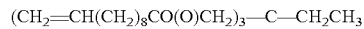

and

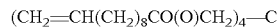

in the presence of a suitable hydrosilylation catalyst.

2. A silicone resin of claim 1 wherein said undecylenic ester compounds is

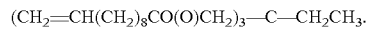

3. A silicone resin of claim 1 wherein said undecylenic ester compounds is

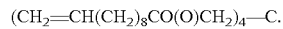

4. A silicone resin of claim 2 wherein x is an integer ranging from 1 to 200; and y is an integer ranging from 4 to 20.

5. A silicone resin of claim 3 wherein x is an integer ranging from 1 to 200; and
y is an integer ranging from 4 to 20.

6. A silicone resin of claim 2 wherein x is an integer ranging from 1 to 10;
and y is an integer ranging from 4 to 10.

7. A silicone resin of claim 3 wherein x is an integer ranging from 1 to 10;
and y is an integer ranging from 4 to 10.

8. A silicone resin of claim 2 wherein x is 0; and y is an integer ranging from 4 to 10.

9. A silicone resin of claim 3 wherein x is 0; and y is an integer ranging from 4 to 10.

* * * * *